United States Patent

Bencsits

[11] Patent Number: 5,991,507
[45] Date of Patent: Nov. 23, 1999

[54] VAPORIZER

[75] Inventor: Franz Bencsits, Zurich, Switzerland

[73] Assignee: Perycut-Chemie AG, Zurich, Switzerland

[21] Appl. No.: 08/913,693

[22] PCT Filed: Jan. 19, 1996

[86] PCT No.: PCT/EP96/00229

§ 371 Date: Nov. 6, 1997

§ 102(e) Date: Nov. 6, 1997

[87] PCT Pub. No.: WO96/28969

PCT Pub. Date: Sep. 26, 1996

[30] Foreign Application Priority Data

Mar. 20, 1995 [DE] Germany ............ 295 04 734 U

[51] Int. Cl.$^6$ ............... F24F 6/08; B01D 47/16
[52] U.S. Cl. ............................. 392/395; 261/99
[58] Field of Search ............... 392/386, 390, 392/392, 394, 395; 122/366, 242; 261/94, 99, 100, 104, DIG. 65

[56] References Cited

U.S. PATENT DOCUMENTS

| | | | |
|---|---|---|---|
| 2,616,024 | 10/1952 | Laibow | 392/392 |
| 2,931,880 | 4/1960 | Yaffe | 392/392 |
| 4,214,146 | 7/1980 | Schimanski | 392/392 |
| 4,266,116 | 5/1981 | Bauer et al. | 392/395 |
| 4,467,177 | 8/1984 | Zobele | 392/392 |
| 4,748,314 | 5/1988 | Desage | 392/395 |
| 5,602,958 | 2/1997 | Vergnes | 392/390 |

FOREIGN PATENT DOCUMENTS

| | | |
|---|---|---|
| 0 249 926 | 12/1987 | European Pat. Off. . |
| 37 37 272 A1 | 11/1987 | Germany . |
| 90 14 309 U | 10/1990 | Germany . |
| 2192337 | 1/1988 | United Kingdom . |

*Primary Examiner*—Teresa Walberg
*Assistant Examiner*—Sam Paik
*Attorney, Agent, or Firm*—Nilles & Nilles SC

[57] ABSTRACT

An evaporator (1) for evaporating volatile liquids (2), in particular liquid insecticides, has a container (3) for the liquid (2), a wick (4) that takes up the liquid and a heating element associated to the wick. In order to improve such an evaporator so that it is easier to handle and at the same time completely evaporates the liquid in the container, the wick is spaced apart from the container and is connected thereto by a liquid supply duct.

23 Claims, 2 Drawing Sheets ized liquids, especially liquid insecticides, com-
VAPORIZER

BACKGROUND OF THE INVENTION

1. Field of the Invention

The present invention refers to a vaporizer for vaporizing highly volatile liquids, especially liquid insecticides, comprising a receptacle for said liquid, a wick absorbing said liquid, and a heating element associated with said wick.

2. Description of the Related Art

A vaporizer of this type is known from DE 37 37 272 C2. In the case of this known vaporizer, a receptacle is arranged in a housing, said receptacle being introduced in the housing from below and being adapted to be secured therein e.g. by means of screws. The receptacle is filled with a highly volatile liquid, especially a liquid insecticide. For vaporizing the liquid by heating, a wick is inserted in said receptacle through an upper opening, an upper end of said wick projecting beyond the receptacle, whereas the lower end thereof is immersed in the liquid. A heating element is arranged the upper end of the wick the heating element surrounds said wick and which heats an upper portion thereof so as to vaporize the liquid sucked up from the receptacle.

This known vaporizer is disadavantageous insofar as it is comparatively difficult to refill the receptacle because said receptacle must be removed from the housing together with the wick. Furthermore, the wick must be removed from the upper end of the receptacle so that additional liquid can be poured into the receptacle. For this purpose, the wick can, for example, be secured in position in a separate holder attachment, which is adapted to be screwed onto the upper end of the receptacle. Analogously, a renewed insertion of the wick and of the receptacle into the housing, when the receptacle has been refilled, is comparatively complicated.

Furthermore, it is also disadvantageous that the lower end of the wick has to be positioned accurately so as to suck up the liquid in the receptacle completely. When the lower end of the wick is positioned at a distance from the receptacle base, a liquid residue that cannot be used will remain in the receptacle.

OBJECTS AND SUMMARY OF THE INVENTION

Hence, it is the object of the present invention to improve a vaporizer of the type mentioned at the beginning in such a way that it can be handled more easily and that it can simultaneously be guaranteed that the liquid contained in the receptacle can be vaporized completely.

This object is achieved in that the wick is arranged in spaced relationship with said receptacle and is connected thereto via a supply line used for supplying the liquid.

In this way, the receptacle can be handled and filled independently of the wick. The receptacle can be filled without being removed from a respective housing, since, in contrast to e.g. DE 37 37 272 C2, no wick projects beyond the upper end of the receptacle. In addition, it is no longer necessary to position the wick in the receptacle in such a way that the liquid can be sucked up completely. The wick is now supplied with said liquid via the supply line until the receptacle is completely empty. A further advantage is that the vaporizer according to the present invention is ready for use within a shorter period of time because the liquid need not be transported along the whole wick towards the heating element by means of the capillary action or the like. The liquid flows via the supply line within a comparatively short period of time directly to the wick, which has, in comparison with DE 37 37 272 C2, comparatively small dimensions.

In order to guarantee that the receptacle empties completely in the most simple manner, the wick is arranged below the receptacle. In this way, the liquid can flow automatically to the wick without further aids, such as pumps or the like being required.

The wick can be produced from various materials in a manner known per se. Such materials are, for example, various fibers, such as felt, cotton or the like. The wick is preferably made from an inorganic, porous material. Such materials are ceramics, glass fibres, plaster, bentonite, kaoline, talcum, diatomaceous earth, perlite, etc. The wick can be produced by pressing a powder consisting of one or more of these materials.

For producing the wick in a simple manner and for obtaining simultaneously comparatively large surfaces for vaporizing the liquid, the wick consists preferably of a substantially cuboid vaporizer body.

In this connection, it will also be advantageous when the heating element is associated with a bottom surface of the vaporizer body, which is located opposite the top surface of said vaporizer body that gives off the vaporized liquid, and when the supply line is connected to a lateral surface of said vaporizer body. The vaporizer body has thus supplied thereto liquid via a lateral surface, the bottom surface thereof is heated and the top surface thereof gives off the vaporized liquid. Normally, the top and bottom surfaces have dimensions which are larger than those of the lateral surface so that the liquid can be heated and vaporized simply and rapidly. At the same time, the vaporizer body can be comparatively compact.

The vaporizer body is provided with a projection which is adapted to be inserted into a first end of the supply line so that said supply line can easily be connected to the lateral surface of the vaporizer body. Said projection preferably consists of the same material as the vaporizer body.

For holding the vaporizer body in a simple manner, at least the bottom surface of said vaporizer body rests on a heat-conducting support plate having the heating element arranged thereon. In view of the fact that the support plate is heat-conducting, the heating element can be smaller than the bottom surface of the vaporizer body. The heat produced by the heating element is transferred by the support plate to the whole bottom surface of the vaporizer body. It follows that uniform heating and, consequently, a uniform vaporization on the whole top surface of the vaporizer body, can take place.

In this connection, it will be advantageous when the heating element is arranged on a bottom surface of the support plate located opposite the vaporizer body. The heat will thus be transferred directly through the support plate to the bottom surface of the vaporizer body.

In correspondence with DE 37 37 272 C2, the receptacle and the vaporizer body can be arranged in a housing in the case of the vaporizer according to the present invention. In addition, the receptacle can releasably be secured to said housing. In order to achieve simple fastening and also a simple release of the receptacle, locking elements project from the receptacle and counterlocking elements are formed on the housing, said counterlocking elements being adapted to be brought into locking engagement with said locking elements.

The locking elements and the counterlocking elements can be implemented in many different ways. In accordance with a preferred embodiment, the locking elements are implemented as locking hooks projecting from a bottom surface of the receptacle, said locking hooks engaging locking apertures provided as counterlocking elements in a reception surface for the bottom surface of the receptacle, said reception surface being formed on the housing. The receptacle is in this way simply placed onto the reception surface from above and lockingly engaged therewith.

For securing the supply line in position on the receptacle at an advantageous location and in a simple manner, a connection pin projects from the bottom surface of said receptacle, the connection pin is adapted to have attached thereto a second end of the supply line, and an opening, which is complementary to said connection pin, is formed in the reception surface. The connection pin can, consequently, be inserted into the associated opening when the receptacle is brought into locking engagement with the reception surface. The vaporizer body can be arranged below this reception surface and, if desired, can also be laterally displaced relative to the receptacle such that the supply line extends between the connection pin and the projection of the vaporizer body.

In order to permit the reception surface and the receptacle to be associated more easily with each other, the reception surface is provided with a circumferential rim projecting upwards in the direction of the receptacle and forming at least along one side of said receptacle a stop wall having a height that corresponds essentially to a receptacle height. The side of the receptacle associated with the stop wall abuts on said stop wall. The stop wall can be implemented as a flat or as a curved wall. Preferably, the receptacle is substantially box-shaped.

In order to permit simple filling of the receptacle, said receptacle has at the upper end thereof a filling hole surrounded by a substantially horizontal rim. A lid, which is adapted to be pushed onto said filling hole, has a push-on groove which is complementary to said rim. By means of this special structural design of the lid, inadvertent opening of said lid, e.g. by children, is prevented so that children cannot come into contact with the liquid.

In accordance with one embodiment of the present invention, the lid can be provided with a flange projecting in the direction of the stop wall, said flange being inserted in an aperture formed at the upper end of said stop wall when the lid has been pushed onto said filling opening. This flange can be used as a handling means for releasing the lid.

In this connection, it will also be advantageous when two locking bevels project from the stop wall in said aperture and when the lid flange is provided with complementary locking projections that engage behind said locking bevels. Due to this arrangement, it is so difficult to remove the lid that at least small children will not be able to remove the lid from the receptacle. An inadvertent removal of the lid is prevented as well.

The locking projections protrude from the lid flange laterally and horizontally so that, in spite of the above-mentioned arrangement, the lid can be removed from the receptacle comparatively easily. A front end of the lid flange can be engaged from below for opening the lid, whereby the locking engagement between the locking projection and the locking bevel will be eliminated so that the lid can be removed along the edge of the opening.

For obtaining an outwardly closed housing and for permitting all the necessary parts to be inserted into the housing in a simple manner when the vaporizer is being produced, the housing comprises an upper housing component and a lower housing component, wall sections of said upper and lower housing components which face each other engaging one behind the other.

The upper and lower housing components are provided with complementary locking means so that additional means, such as screws or the like, for connecting the two housing components can be dispensed with in this connection. These complementary locking means are in engagement with one another in the assembled condition of the housing.

The housing has arranged thereon a plug unit so that the vaporizer can be connected to a socket in a simple manner. In this respect, it will be advantageous when the plug unit is supported in the upper housing component and/or in the lower housing component such that it is adapted to be rotated by an angle of at least 90°. This permits the vaporizer to be used for sockets having horizontally juxtaposed plug contacts as well as for sockets having vertically superimposed plug contacts, without any liquid escaping from the receptacle. The rotational angle can be limited by suitable stops on the plug unit and/or on the housing, one stop corresponding to the horizontal and another one to the vertical arrangement of the plug contacts of the socket.

It will also be advantageous when the plug unit is electrically connected to the heating element via a switch and an indicator lamp so that the vaporizer can easily be actuated and so that the operating condition of said vaporizer can be seen simultaneously. The switch can, for example, be a toggle switch controlling two different operating conditions of the vaporizer. The operating conditions normally differ with regard to the heating power of the heating element. The indicator lamp used is preferably an LED indicator lamp. This lamp can be arranged essentially at any position of the housing. If the receptacle consists e.g. of a transparent material, the indicator lamp may also be arranged in the reception surface so that it can be seen through the receptacle.

The housing and the receptacle are preferably produced from an electrically insulating material, such as plastic or the like.

BRIEF DESCRIPTION OF THE DRAWINGS

In the following, an advantageous embodiment of the present invention will be explained and described in detail on the basis of the figures enclosed in the drawing, in which.

DESCRIPTION OF THE PREFERRED EMBODIMENTS

Figure 1:
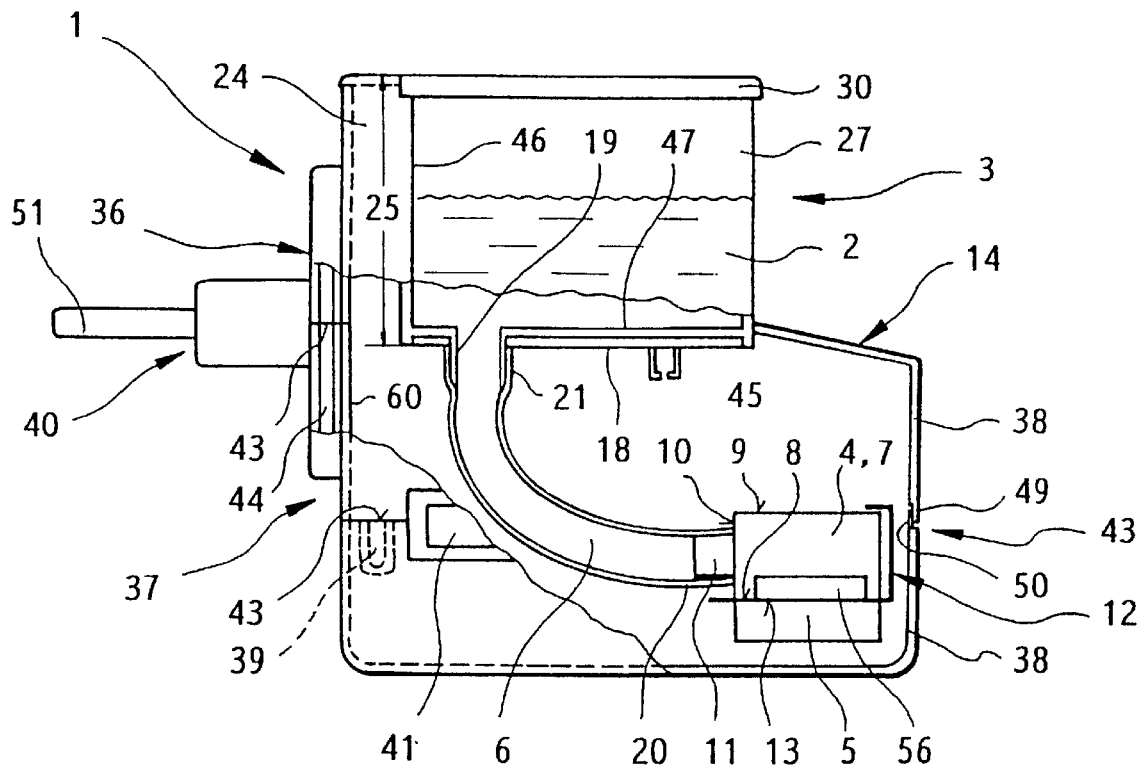
FIG. 1 shows a side view, partially broken away, of a vaporizer according to the present invention.

In the side view of a vaporizer 1 according to FIG. 1, said vaporizer comprises a receptacle 3 containing a liquid 2, and a housing 14. The receptacle 3 is attached to a flat reception surface 18 of the housing 14 from above. The contour of the reception surface 18 corresponds to the cross-section of the receptacle, cf. also FIG. 2. The receptacle is closed by a lid 30 at the upper end thereof, said lid being adapted to be pushed onto the receptacle from the right towards the left in FIG. 1. The lid closes a filling hole, which is formed at the upper end 27 of the receptacle, and extends up to a stop wall 24. This stop wall 24 substantially forms part of a rim surrounding the reception surface 18, and it extends at right angles to said reception surface 18. The receptacle 3 is adapted to be attached to the reception surface 18 from above; in the attached condition, the receptacle 3 is laterally held by the rim 23, cf. FIG. 2, and by wall projections 46 projecting from the stop wall 24 on both sides thereof, cf. again FIG. 2.

Figure 3:
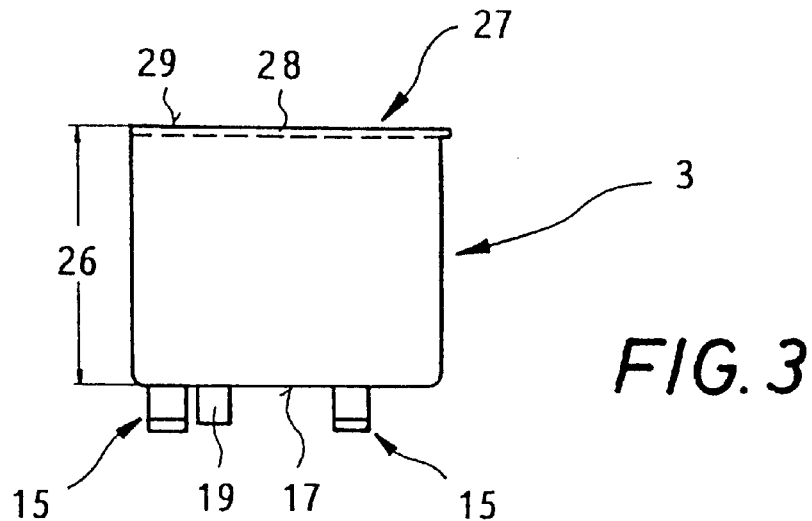
FIG. 3 shows a side view of a receptacle that has been removed from the vaporizer according to FIG. 1.

The stop wall 24 has a height 25 corresponding essentially to a receptacle height 26 according to FIG. 3. The height of the wall exceeds the height of the receptacle to such an extent that the lid 30 is arranged flush with the upper end of the stop wall 24.

The receptacle base 47 has formed thereon a connection pin 19 having substantially the shape of a hollow cylinder. This connection pin extends through the an opening 22 of the reception surface 18, cf. also FIG. 2, up to and into the housing 14. The connection pin 19 has attached thereto a second end 21 of a supply line 6 whose opposite first end 20 is attached to a pinlike projection 11 of a vaporizer body 7 acting as a wick. The vaporizer body 7 is cuboid and comprises an top surface 9, a bottom surface 8 and four lateral surfaces 10 joining the top and bottom surfaces 8, 9. The projection 11 protrudes from a lateral surface 10 of the vaporizer body 7 which faces the supply line.

A support plate 12 is arranged in the housing 14 for holding the vaporizer body 7. This support plate 12 has a substantially horizontal support surface on which the vaporizer body 7 rests. The vaporizer body 7 is laterally held by lateral walls 56, whereas the back of said vaporizer body 7, which is located opposite the projection 11, is held by a rear wall having at the upper end thereof at least two holding tongues which are bent onto the top surface 9 of the vaporizer body 7. With regard to a more detailed representation of the support plate 12, reference is made to FIG. 5.

The housing 14 is composed of an upper housing component 36 and of a lower housing component 37. The two housing components meet along a connection line 43. In the area of this connection line, wall noses 49 and 50, respectively, which are thinner than the rest of the wall thickness and which engage one behind the other, project from wall sections 38 of the housing components that face each other.

In the area of the connection line 43, a switch 41 is provided. For accommodating and fastening the switch, recesses are formed in a manner known per se in the wall sections of the housing components facing each other.

For connecting the two housing components, locking means 39 are provided. These locking means comprise locking clips projecting e.g., from the upper housing component 36 and locking protrusions arranged in the lower housing component 37 on the inner surface thereof.

One side of the vaporizer 1 has arranged thereon a plug unit 40 with two contact fingers 51. The plug unit 40 is held in a substantially circular rotary guide means consisting of two halves which are each defined by one of the housing components. The rotary guide means is provided with a rotary groove 44 in which the plug unit 40 is rotatably supported. For forming the rotary guide means, a front wall 60 projects upwards from the lower housing component 37 at the housing component end facing the plug unit 40. This front wall 60 has formed thereon one half of the rotary guide means including the respective rotary groove 44.

In the area of the reception surface 18, an LED holder 45 is arranged. This LED holder serves to hold an LED indicator lamp, which is not shown; the LED indicator lamp is visible through a suitable opening in the reception surface 18 through the receptacle 3 produced from a transparent material.

Figure 2:
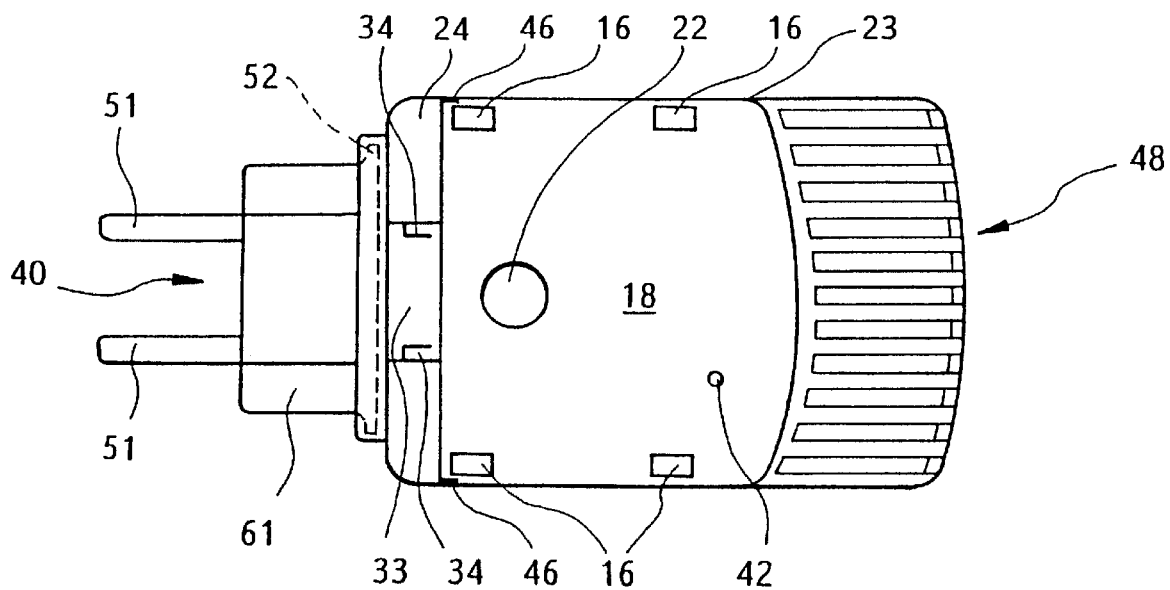
FIG. 2 shows a top view of the vaporizer according to FIG. 1 in a condition in which the receptacle has been removed.

In FIG. 2, a top view of the vaporizer according to FIG. 1 is shown. Identical components are designated by identical reference numerals and part of these reference numerals is also mentioned.

To make things easier, the receptacle 3 is not shown in FIG. 2 and, consequently, the reception surface 18 can be seen, which includes four locking apertures 16 implemented as counterlocking elements, one opening 22 for the connection pin 19 of the receptacle 3, cf. FIG. 1, and one opening 42 for the LED indicator lamp. The reception surface 18 has a substantially rectangular contour, a reception surface side facing a plurality of venting slots 48 having an outward convex curvature. The reception surface 18 is surrounded by a circumferential rim 23 projecting upwards in the direction of the receptacle beyond the reception surface 18 along the circumference thereof. On the side facing the plug unit 40, this circumferential rim 23 defines the stop wall 24. This stop wall 24 is provided with wall projections 46 projecting on both sides thereof in the direction of the reception surface 18, the receptacle, which is not shown in FIG. 2, being held between these wall projections 46 and the upwardly projecting circumferential rim 23. The stop wall 24 is provided with an aperture 33 at the upper end thereof. This aperture 33 has a rectangular contour, ramp-shaped locking bevels 34 being formed along the shorter sides of the rectangle. These locking bevels 34 increase in height towards the plug unit 40. On the outer side of the stop wall 24 located opposite the reception surface 18, the rotary guide means including the groove 44 according to FIG. 1 are arranged. The plug unit 40, including a radially projecting edge flange 52, is rotatably supported in these rotary guide means. An insertion element 61 for insertion in a socket of the plug unit 40 projects beyond the rotary guide means, two contact fingers 51 projecting beyond the insertion element 61.

FIG. 3 shows a side view of the receptacle 3. This receptacle 3 is provided with a number of locking hooks 15, which project from the bottom surface 17 of the receptacle base and which are implemented as locking elements, and with the connection pin 19. The bottom surface 17 of the receptacle, the locking hooks 15 and the connection pin 19 are implemented and arranged in such a way that they are adapted to be attached to the reception surface 18 and to be inserted into the locking apertures 16 and the opening 22, respectively.

At the upper end 27 of the receptacle 3, a filling hole 29 is formed, which is surrounded by a rim 28 projecting outwardly and horizontally beyond the receptacle.

Figure 4:
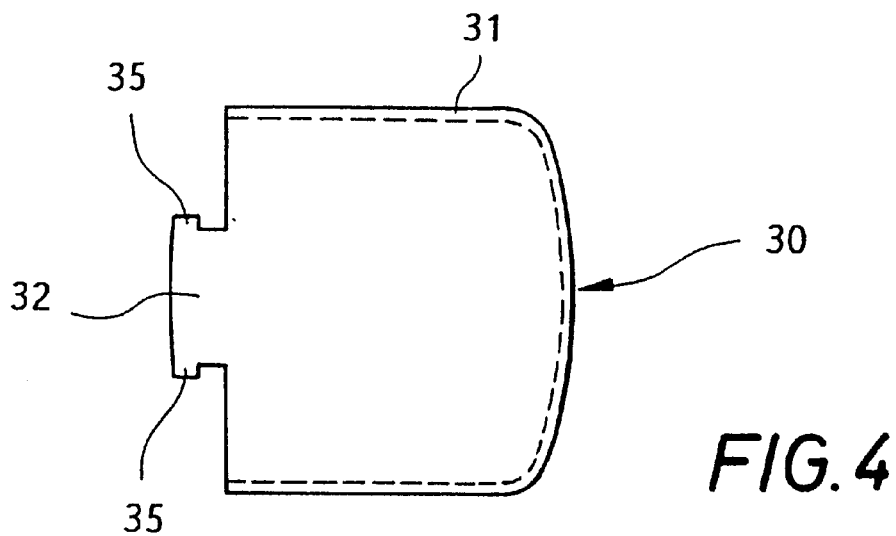
FIG. 4 shows a top view of a lid which is adapted to be pushed onto the receptacle.

In FIG. 4, a top view of the lid 30 is shown. This lid 30 has a shape corresponding to the contour of the upper end 27 of the receptacle 3. The lid is provided with a push-on groove 31 formed along the edge thereof. This push-on groove is formed in that the edge of the lid is first bent downwards and then inwards, the groove being formed between the inwardly bent part and the top surface of the lid 30. On the side facing the stop wall 24 according to FIG. 1 and 2, the lid 30 is not provided with any push-on groove 31. Instead of a push-on groove, a flange 32 is formed on this side, a respective locking projection 35 protruding on each side of the flange 32. These locking projections 35 slide over the locking bevels 34 according to FIG. 2 when the lid 30 is being pushed onto the receptacle 3. When the lid has reached its fully closed position, the locking projections 35 engage behind the locking bevels 34 so as to secure the lid 30 at its closed position.

Figure 5:
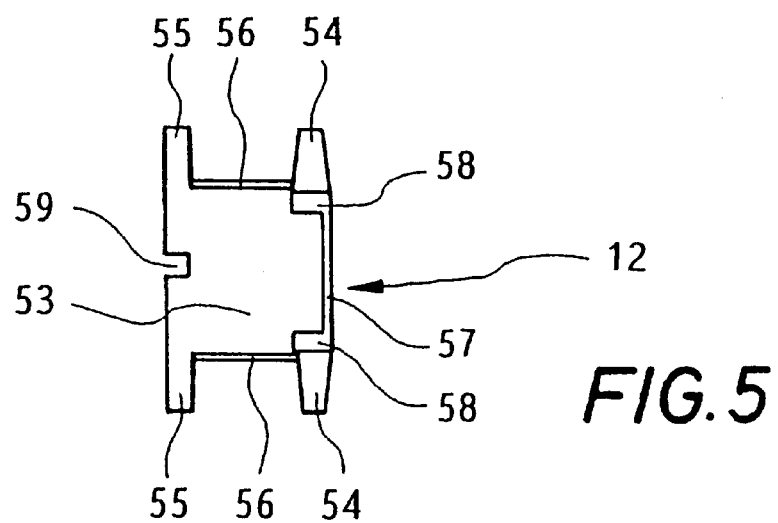
FIG. 5 shows a top view of a support plate for a vaporizer, said support plate being shown in FIG. 1.

FIG. 5 shows a support plate 12 according to FIG. 1 without the vaporizer body 7. The support plate 12 is produced from a heat-conducting material, such as a steel plate or the like. It has a flat support surface 53 onto which the vaporizer body can be placed. For laterally holding the vaporizer body, two lateral walls 56 project upwards from the support surface 53, cf. also FIG. 1. For holding a rear end of the vaporizer body, a rear wall 57 additionally projects upwards from support surface 53. The lateral walls 56 and the rear wall 57 simultaneously form an edge of the support surface 53. Normally, the height of the rear wall 57 exceeds that of the lateral walls 56. The rear wall 57 has two holding tongues 58 at the upper end thereof, the holding tongues 58 being arranged essentially parallel to the support surface 53. According to FIG. 1, these holding tongues 58 rest on the top surface 9 of the vaporizer body 7.

Support fingers 54 and 55 project from the support surface 53 at both ends of the lateral walls 56, said support fingers extending in the longitudinal direction of the rear wall 57. These support fingers are used for fastening the support plate 12 in the housing 14 according to FIG. 1. The fastening can be effected by four projections, which protrude from the upper housing component and rest on said support fingers 54 and 55 from above, and by four complementary projections, which protrude from the lower housing component and rest on said support fingers 54 and 55 from below, the support fingers being clamped between these projections in the locked condition of the housing components.

For holding the heating element 5 according to FIG. 1 on the bottom side of the support surface 53, a front portion of the support surface 53 is bent downwards thus forming a recess 59. The front portion engages the heating element 5 from below, whereby said heating element is pressed onto the bottom side 13 of the support plate 12, cf. FIG. 1.

I claim:

1. A vaporizer for vaporizing a highly volatile liquid, said vaporizer comprising: a receptacle for storing the liquid, a wick which is configured to absorb the liquid, and a heating element associated with said wick, wherein said wick is arranged in spaced relationship with said receptacle and is connected thereto via a supply line for supplying the liquid, wherein at least a portion of said wick forms a vaporizer body, said vaporizer body having a bottom surface which is heated by the heating element to vaporize the liquid, and having a top surface which is located opposite the bottom surface and which gives off vaporized liquid, and wherein the supply line is connected to a lateral surface of said vaporizer body.

2. A vaporizer according to claim 1, wherein the wick is arranged below the receptacle.

3. A vaporizer according to claim 2, wherein the wick is made form an inorganic, porous material.

4. A vaporizer according to claim 3, wherein the vaporizer body is substantially cuboid.

5. A vaporizer according to claim 4, wherein said lateral surface of said vaporizer body has a projection which is adapted to be inserted into a first end of the supply line.

6. A vaporizer according to claim 1, wherein at least the bottom surface of the vaporizer body rests on a heat-conducting support plate having the heating element arranged thereon.

7. A vaporizer according to claim 6, wherein the heating element is arranged on a bottom side of the support plate located opposite the vaporizer body.

8. A vaporizer according to claim 5, further comprising a housing for receiving the receptacle, the vaporizer body, the support plate and the heating element, said receptacle being releasably secured to said housing, wherein locking elements project from the receptacle, and wherein counterlocking elements are formed on the housing, said counterlocking elements being adapted to be brought into locking engagement with said locking elements.

9. A vaporizer according to claim 8, wherein the locking elements are implemented as locking hooks projecting from a bottom surface of the receptacle, and the counterlocking elements are locking apertures provided in a reception surface for the bottom surface of the receptacle, said reception surface being formed on the housing.

10. A vaporizer according to claim 9, wherein a connection pin projects from the bottom surface of said receptacle, said connection pin being adapted to have a second end of the supply line attached thereto, an opening, which is complementary to said connection pin, being formed in said reception surface.

11. A vaporizer according to claim 9, wherein the reception surface is provided with a circumferential rim projecting upwards in the direction of the receptacle and forming, at least along one side of said receptacle, a stop wall having a height that corresponds essentially to a receptacle height.

12. A vaporizer according to claim 1, wherein the receptacle has, at an upper end thereof, a filling hole surrounded by a substantially horizontal rim, and a lid, said lid being adapted to be pushed onto said filling hole and having a push-on groove which is complementary to said rim.

13. A vaporizer according to claim 12, wherein the lid is provided with a flange projecting in the direction of the stop wall, said flange being inserted in an aperture formed at the upper end of said stop wall when the lid has been pushed onto said filling opening.

14. A vaporizer according to claim 13, wherein two locking bevels project from the stop wall in said aperture and the lid flange is provided with complementary locking projections which engage behind said locking bevels.

15. A vaporizer according to claim 14, wherein the locking projections protrude form the lid flange laterally and horizontally.

16. A vaporizer according to claim 8, wherein the housing comprises an upper housing component and a lower housing component, and wherein wall sections of said upper and lower housing components face each other and engage one behind the other.

17. A vaporizer according to claim 16, wherein the upper and lower housing components are provided with complementary locking structures.

18. A vaporizer according to claim 16, wherein a plug unit is supported in at least one of the upper housing component and in the lower housing component such that the plug unit is adapted to be rotatable through an angle of at least 90°.

19. A vaporizer according to claim 18, wherein the plug unit is electrically connected to the heating element via at least one switch and an indicator lamp.

20. A vaporizer according to claim 11, wherein the receptacle has, at an upper end thereof, a filling hole surrounded by a substantially horizontal rim and a lid, said lid being adapted to be pushed onto said filling hole and having a push-on groove which is complementary to said rim.

21. A vaporizer for vaporizing a volatile liquid, said vaporizer comprising:
a receptacle which is configured to store the liquid;
a heating element;

a wick which is spaced apart from said receptacle and which is configured to absorb the liquid, wherein said wick forms a vaporizer body, said vaporizer body having a lateral surface, a bottom surface which is heated by said heating element, and a top surface which gives off vaporized liquid; and a supply line which connects said receptacle to said lateral surface of said vaporizer body.

22. A vaporizer for vaporizing a volatile liquid, said vaporizer comprising:

a receptacle which is configured to store the liquid;

a heat conducting support plate;

a heating element which is disposed on said support plate;

a wick which is spaced apart from said receptacle and which is configured to absorb the liquid, wherein said wick forms a vaporizer body, said vaporizer body having a bottom surface which rests on said support plate; and a supply line which connects said receptacle to said vaporizer body.

23. A vaporizer according to claim 22, wherein said heating element is arranged on a bottom side of said support plate and said vaporizer body is supported on a top side of said support plate.

* * * * *